US012805910B2

(12) United States Patent
Allen et al.

(10) Patent No.: US 12,805,910 B2
(45) **Date of Patent: *Nov. 24, 2026**

(54) MINIMALLY INVASIVE SURGERY GUIDE WIRE CAPTURING INSTRUMENTATION

(71) Applicant: GLOBUS MEDICAL, INC., Audubon, PA (US)

(72) Inventors: Caelan Allen, Ambler, PA (US); Matthew Bechtel, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/234,369

(22) Filed: Jun. 11, 2025

(65) Prior Publication Data

US 2025/0302506 A1 Oct. 2, 2025

Related U.S. Application Data

(63) Continuation of application No. 17/815,018, filed on Jul. 26, 2022, now Pat. No. 12,329,418.

(51) Int. Cl.
*A61B 17/70* (2006.01)

(52) U.S. Cl.
CPC ...... *A61B 17/7032* (2013.01); *A61B 17/7035* (2013.01)

(58) Field of Classification Search
CPC ........................ A61B 17/7032; A61B 17/7035
See application file for complete search history.

(56) References Cited

U.S. PATENT DOCUMENTS

| | | | | |
|---|---|---|---|---|
| 6,827,722 | B1 | 12/2004 | Schoenefeld | |
| 7,207,995 | B1 | 4/2007 | Vanderwalle | |
| 8,192,402 | B2 | 6/2012 | Anderson et al. | |
| 8,641,717 | B2 | 2/2014 | Defossez et al. | |
| 8,715,293 | B2 | 5/2014 | Vanderwalle | |
| 9,186,484 | B2 | 11/2015 | Defossez et al. | |
| 9,254,160 | B2 * | 2/2016 | Pakzaban | A61B 17/8875 |
| 9,289,249 | B2 | 3/2016 | Ramsay et al. | |
| 9,433,445 | B2 | 9/2016 | Ramsay et al. | |
| 10,194,967 | B2 | 2/2019 | Baynham | |
| 10,413,339 | B2 | 9/2019 | Ramsay et al. | |
| 10,973,558 | B2 | 4/2021 | Kam et al. | |
| 11,344,353 | B2 | 5/2022 | Geist et al. | |
| 2008/0262555 | A1 | 10/2008 | Assell et al. | |
| 2020/0305944 | A1 | 10/2020 | Geist et al. | |
| 2020/0323566 | A1 | 10/2020 | Geist et al. | |
| 2021/0228245 | A1 | 7/2021 | Geist et al. | |
| 2021/0244424 | A1 | 8/2021 | Suchomel et al. | |

* cited by examiner

*Primary Examiner* — Si Ming Ku

(57) ABSTRACT

A surgical instrument includes a driver shaft couplable to a cannulated pedicle screw. The driver shaft having a through bore for conveying a surgical guide wire through the cannulated pedicle screw. The surgical instrument also includes a wire positioning assembly having a positional adjustment mechanism for adjusting an axial position of the surgical guide wire with respect to the cannulated pedicle screw and a locking mechanism for locking the axial position of the surgical guide wire. Additionally, the surgical instrument includes a driver actuator coupled to the driver shaft. The driver actuator is operable to rotate the driver shaft to drive rotation of the cannulated pedicle screw.

17 Claims, 11 Drawing Sheets

MINIMALLY INVASIVE SURGERY GUIDE WIRE CAPTURING INSTRUMENTATION

CROSS REFERENCE TO RELATED APPLICATIONS

This application is a continuation of U.S. patent application Ser. No. 17/815,018 filed on Jul. 26, 2022, which is incorporated in its entirety herein.

BACKGROUND

Pedicle screws may generally be used in spinal fusion surgeries. During operation, the pedicle screws may be inserted into damaged segments (e.g., vertebrae) of the spine. Once inserted, metal rods may then be connected to the pedicle screws to hold the vertebrae and bone graft in place so that the damaged segments may fuse together. In some operations, cannulated pedicle screws may be used in combination with surgical guide wire. Generally, the surgical guide wire is first inserted into a vertebra using an instrument (e.g., guide wire introducer). Once the guide wire is inserted, the guide wire introducer is disconnected, and a cannulated screw may be inserted over the guide wire and directed to a particular location of the vertebra via the surgical guide wire. With the cannulated pedicle screw correctly positioned with respect to the vertebra, a driver or drill is used to drive the cannulated pedicle screw into the vertebra. Using surgical guide wire is especially beneficial for minimally invasive surgeries as there may be low visibility for a surgeon inserting the pedicle screw. Having the surgical guide wire direct the pedicle screw may help ensure proper placement of the pedicle screw. However, this process may be time consuming. As prolonged operative time may be associated with an increased risk of complications, new instrumentation is needed to streamline the technique.

BRIEF DESCRIPTION OF THE DRAWINGS

These drawings illustrate certain aspects of some of the embodiments of the present invention and should not be used to limit or define the invention.

DETAILED DESCRIPTION

It is to be understood that the present disclosure is not limited to particular systems, devices, and/or methods, which may, of course, vary. It is also to be understood that the terminology used herein is for the purpose of describing particular embodiments only and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms “a”, “an”, and “the” include singular and plural referents unless the content clearly dictates otherwise. Furthermore, the word “may” is used throughout this application in a permissive sense (i.e., having the potential to, being able to), not in a mandatory sense (i.e., must). The term “include,” and derivations thereof, mean “including, but not limited to.” The term “coupled” means directly or indirectly connected. If there is any conflict in the usages of a word or term in this specification and one or more patent or other documents that may be incorporated herein by reference, the definitions that are consistent with this specification should be adopted for the purposes of understanding this invention.

Pedicle screws may be inserted or implanted in the thoracolumbar and sacral spine region to treat conditions such as degenerative disc disease, spondylolisthesis, trauma (e.g., fracture or dislocation), tumors, or some combination thereof. As set forth above, cannulated pedicle screws may generally be used in combination with surgical guide wire. The surgical guide wire is first inserted into the vertebrae using an instrument (e.g., guide wire introducer). Once the guide wire is inserted, the guide wire introducer is disconnected, and a cannulated screw may be inserted over the guide wire and directed to a particular location of vertebral bone via the surgical guide wire. With the cannulated pedicle screw correctly positioned with respect to the vertebrae, a driver or drill is used to drive the cannulated pedicle screw into the vertebra. Although using cannulated pedicle screws with surgical guide wire is beneficial for minimally invasive surgeries, the implant or insertion process may be time consuming, which may prolong operation time and lead to an increased risk of complications. To address this issue, a surgical instrument system, as set forth in detail below, may be used to insert a cannulated pedicle screw with an embedded guide wire. Further, the surgical instrument system may be used to capture, release, advance and retract the surgical guide wire, or alternatively a stylet, with respect to the cannulated pedicle screw.

Figure 1:
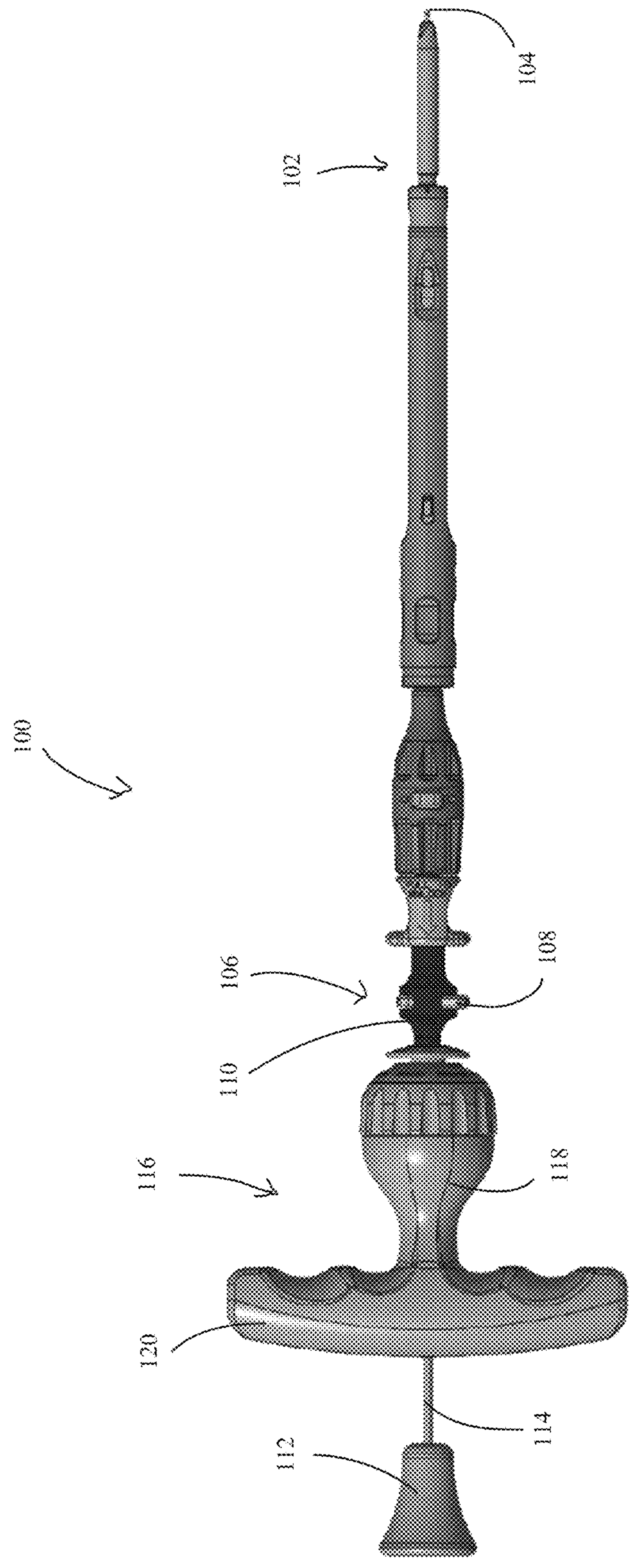
FIG. 1 illustrates a side view of a surgical instrument for inserting a cannulated pedicle screw and a surgical guide wire.

FIG. 1 illustrates a side view of a surgical instrument 100 for inserting a cannulated pedicle screw 102 and a surgical guide wire 104. As illustrated, the surgical guide wire 104 may be extend into and through the cannulated pedicle screw 102. The surgical guide wire 104 may be conveyed along a through bore of the surgical instrument 100 through the cannulated pedicle screw 102 to a desired length and/or conveyed during insertion of the surgical guide wire 104 into the vertebra. The surgical guide wire, inserted into the vertebra, may then guide the cannulated pedicle screw 102 as the surgical instrument 100 is used to drive rotation of the cannulated pedicle screw 102 into the vertebra. Further, the surgical guide wire 104 may be configured to extend and/or retract from the cannulated pedicle screw 102 by sliding along the central bore of the cannulated pedicle screw 102.

As set forth above, a portion of the surgical guide wire 104 protruding from the cannulated pedicle screw 102 may be inserted first into a vertebra during a surgical operation. Optionally, a pilot hole may first be drilled in the vertebra and the pilot hole used to guide placement first of the surgical guide wire before driving the cannulated pedicle screw 102 into the vertebra. In other cases, the cannulated pedicle screw 102 may have a sufficiently sharp leading end to be urged by hand or using the surgical instrument 100 into the vertebra without the need for a pilot hole. As such, the surgical guide wire 104 may be extended with respect to the cannulated pedicle screw 102 such that the surgical guide wire 104 contacts the vertebra before the cannulated pedicle screw 102.

The surgical instrument 100 may include a wire positioning assembly 106 for controlling movement of the surgical guide wire 104 with respect to the cannulated pedicle screw 102, such as to accommodate any of a plurality of different screw sizes, and to advance the surgical guide wire a desired amount ahead of a tip of the cannulated pedicle screw 102. To position the surgical guide wire 104 with respect to the instrument 100, the wire positioning assembly 106 includes a positional adjustment mechanism for adjusting an axial position of the surgical guide wire with respect to the cannulated pedicle screw 102 and a locking mechanism for locking the surgical guide wire in a selected position. In one or more configurations the locking mechanism may include a feature moveable between a locked position and an unlocked position. Specifically, for example, the wire positioning assembly 106 may comprise a wire locking button 108 housed in a wire locking housing 110 and that is actuatable between a locked position and an unlocked position to lock in an axial position of the surgical guide wire 104 once adjusted to the desired position. The wire locking button 108 may interface with the surgical guide wire 104 in the locked position to restrain movement of the surgical guide wire 104. Conversely, the wire locking button 108 may release the surgical guide wire 104 in the unlocked position such that the surgical guide wire 104 may freely move in the axial direction with respect to the cannulated pedicle screw 102.

The wire positioning assembly 106 may also include a wire position handle 112. With the wire locking button 108 in the unlocked position, the wire position handle 112 may actuate (e.g., slide) with respect to the cannulated pedicle screw 102 to move the surgical guide wire 104 with respect to the cannulated pedicle screw 102. The wire position handle 112 may be attached to a push rod 114 that interfaces with a distal end of the surgical guide wire 104. That is, the push rod 114 may be coupled to or otherwise interfaceable with the surgical guide wire 104. As such, actuating the wire position handle 112 may drive the push rod 114 and the push rod 114 may drive the surgical guide wire 104 with respect to the cannulated pedicle screw 102. However, in the locked position, the wire locking button 108 restrains the surgical guide wire 104 such that the wire position handle 112 may not move the surgical guide wire 104. In some embodiments, having the wire locking button 108 in the locked position may also restrain the wire position handle 112.

Moreover, the surgical instrument 100 may also include a driver assembly 116 that interfaces with the cannulated pedicle screw 102. With the surgical guide wire 104 inserted, to position and orient the cannulated pedicle screw 102 with respect to the vertebra, the driver assembly 116 is operable to drive the cannulated pedicle screw 102 into a vertebra (not shown). Specifically, in one or more example, the driver assembly 116 may have a driver shaft 700 (shown in FIG. 7) configured to couple to the cannulated pedicle screw 102. Although it is not explicitly shown in the illustrated embodiment, it is understood that the driver shaft 700 has a through bore for conveying the surgical guide wire 104 therethrough. The surgical guide wire 104 may extend through the wire positioning assembly 106, the driver assembly 116, and the cannulated pedicle screw 102.

The driver assembly 116 may also include a driver actuator 118 coupled to the driver shaft 700. The driver actuator 118 is operable to rotate the driver shaft 700. In this and other examples, the driver actuator 118 includes a handle 120 that is operable to rotate the driver shaft 700 by hand, which transfers a rotational torque to the cannulated pedicle screw 102 to threadedly engage it with the vertebra. More particularly, the driver shaft 700 may be coupled to the cannulated pedicle screw 102 during operation. As such, rotating the driver shaft 700 may rotate the cannulated pedicle screw 102 to drive the cannulated pedicle screw 102 forward into the vertebra or target location. The driver actuator 118 may be actuatable independent of the wire position handle 112. Indeed, the driver actuator 118 may include a driver handle 120 configured to rotate to drive rotation of the driver shaft 700. However, any suitable mechanism may be used to drive rotation of the driver shaft 700.

During operation, the user may push and hold the wire locking button 108 to move the wire locking button 108 to the unlocked position. With the wire locking button 108 in the unlocked position, the user may push the wire position handle 112 axially toward the cannulated pedicle screw 102 until the surgical guide wire 104 is extended to a desired distance with respect to the cannulated pedicle screw 102. The user may then actuate the wire locking button 108 to the locked position and insert the surgical guide wire 104 into the vertebra. In some embodiments, the wire locking button 108 may comprise a spring (not shown) to bias the wire locking button 108 to the locked position. However, the illustrated embodiment, the wire locking button 108 may be toggled between the locked position and the unlocked position. Next, the user may optionally push the wire locking button 108 to slide the cannulated pedicle screw 102 along the surgical guide wire 104 toward the vertebra. Alternatively, the user may forego the preceding step and actuate the driver handle 120 to drive the cannulated pedicle screw 102 into the vertebra. In the illustrated embodiment, rotating the driver handle 120 drives the cannulated pedicle screw 102 axially downward to advance the cannulated pedicle screw 102 along the surgical guide wire 104 and into the vertebra. However, in some embodiments, rotating the driver handle 120 may be configured to drive both the cannulated pedicle screw 102 and the surgical guide wire 104.

Figure 2B:
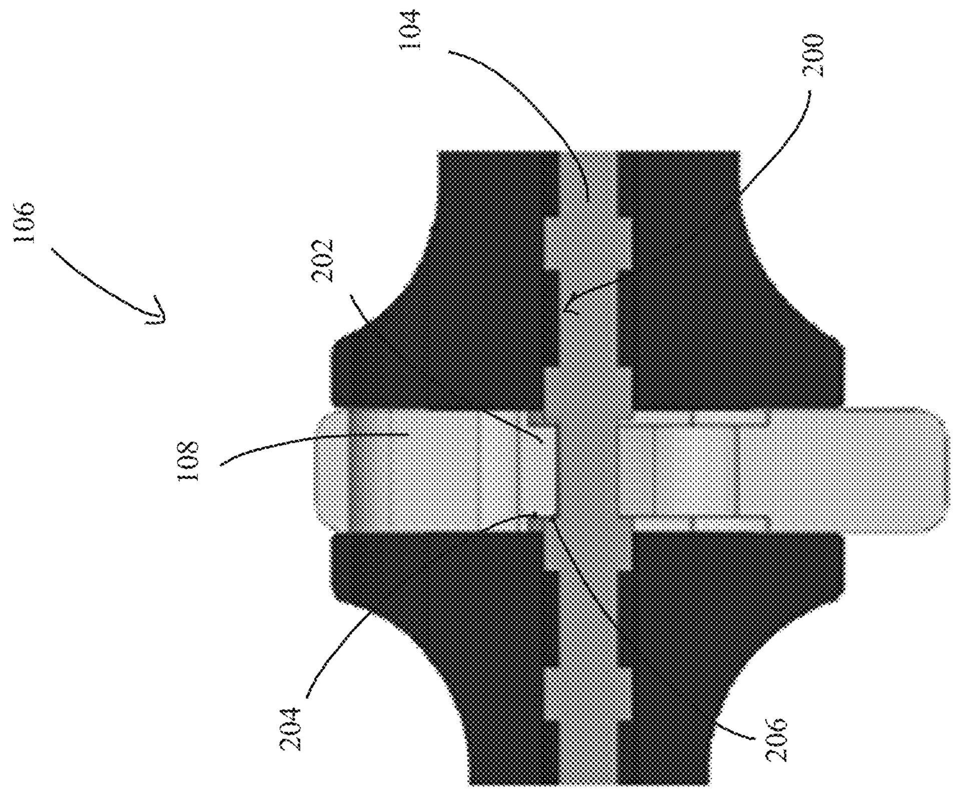
FIGS. 2A & 2B illustrate a side view and a cross-sectional view, respectively, of a wire positioning assembly of the surgical instrument.
Figure 2A:
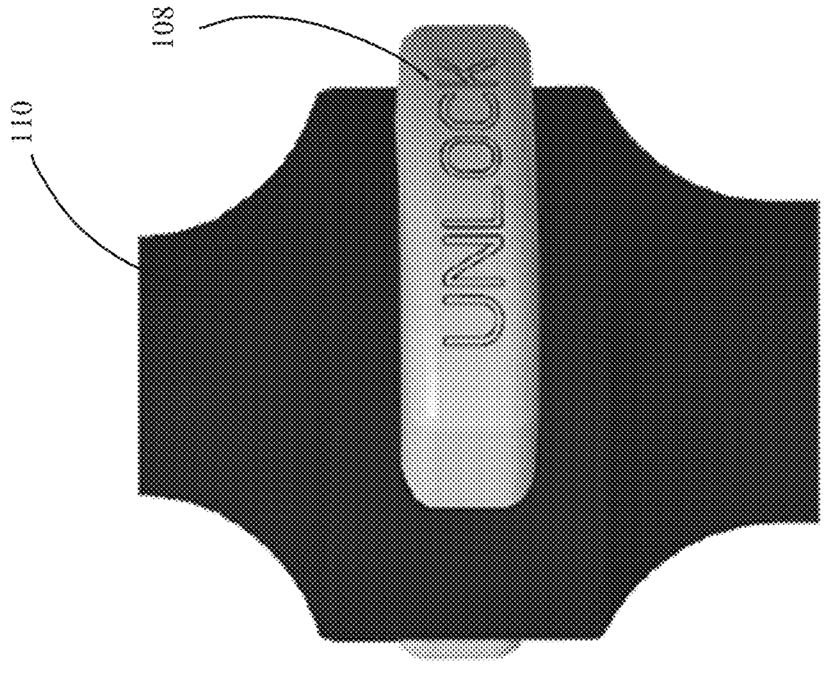

FIGS. 2A & 2B illustrate a side view and a cross-sectional view, respectively, of a wire positioning assembly of the surgical instrument. As illustrated in FIG. 2A, the wire positioning assembly 106 may include the wire locking housing 110 and the wire locking button 108. Referring to FIG. 2B, the wire positioning assembly 106 may further include the surgical guide wire 104, which may be releasably securable via the wire locking button 108. As illustrated, the surgical guide wire 104 may have a plurality of notches 200 axially spaced along a portion of the surgical guide wire 104. The notches 200 may be formed via indentions in the surgical guide wire 104 and/or protrusions from the surgical guide wire 104. Moreover, wherein the wire positioning assembly 106 comprises the wire locking button 108 may be configured to interface with at least one notch of the plurality of notches 200 in the locked position to restrain axial movement of the surgical guide wire 104 with respect to the driver shaft 700. That is, the wire locking button 108 may include a shoulder 202. The shoulder 202 may be sized such that it may fit at least partially with the notches 200 in the surgical guide wire 104 in the locked position. The sidewalls 204 of the shoulder 202 are configured to contact corresponding walls 206 of the notches 200 in the locked position to restrain movement of the surgical guide wire 104. Further, releasing the wire locking button 108 may retract the shoulder 202 from the notch 200 (e.g., the unlocked position) such that the surgical guide wire 104 may slide without contacting the shoulder 202.

In some embodiments, there may be graduations and depth markings on the surgical guide wire 104 to indicate which notch 202 is appropriate to dock for a particular screw length. Indeed, there may be a window in the driver assembly 116 (shown in FIG. 1) and/or the wire positioning assembly 106 such that the depth markings are visible to the user, which may aid in assembly.

Figure 3B:
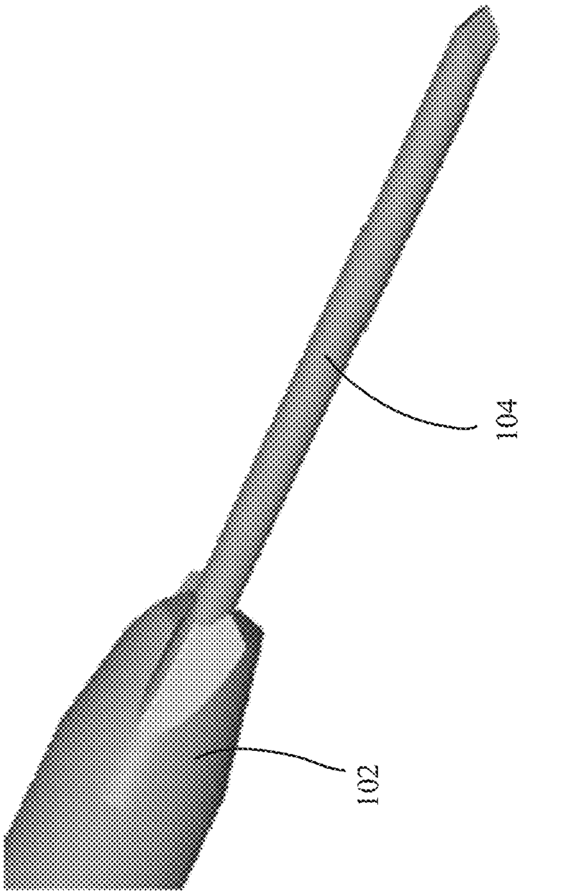
FIGS. 3A & 3B illustrate perspective views of a surgical guide wire in a retracted and an extended position, respectively, with respect to a cannulated pedicle screw.
Figure 3A:
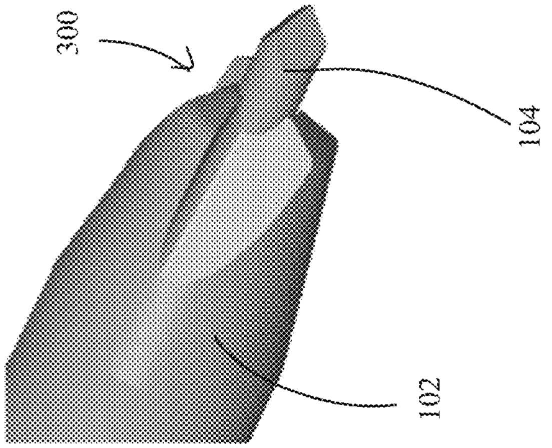

FIGS. 3A & 3B illustrate perspective views of a surgical guide wire in a retracted and an extended position, respectively, with respect to a cannulated pedicle screw. As illustrated in FIG. 3A, the surgical guide wire 104 is disposed in a first position with respect to the cannulated pedicle screw 102. As set forth above, the surgical guide wire 104 is configured to axially extend or retract relative to a tip 300 of the cannulated pedicle screw 102 based at least in part on actuation of the wire positioning assembly 106. Referring to FIG. 3B, the surgical guide wire 104 is disposed in a second position (e.g., an extended position) with respect to the cannulated pedicle screw 102. That is, the surgical guide wire 104 is extended relative to the first position.

Figure 4B:
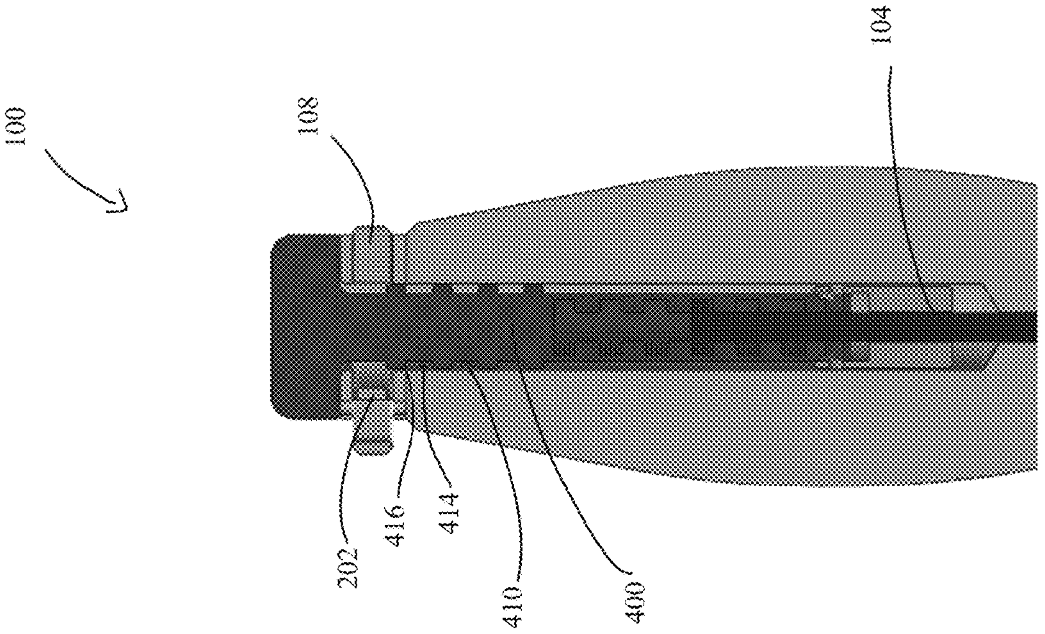
FIGS. 4A & 4B illustrate cross-sectional views of a wire positioning assembly in a retracted position and an extended position, respectively.
Figure 4A:
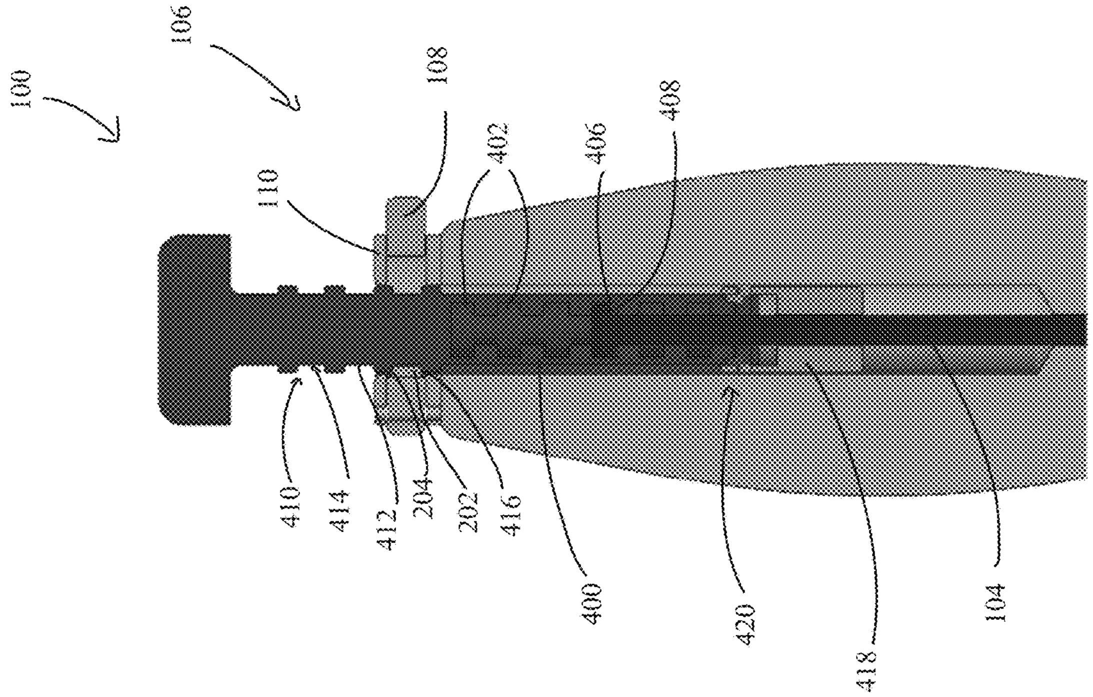

FIGS. 4A & 4B illustrate cross-sectional views of a wire positioning assembly in a retracted position and an extended position, respectively. As illustrated in FIG. 4A, the surgical instrument 100 comprises the wire positioning assembly 106 for controlling movement of the surgical guide wire 104 with respect to the cannulated pedicle screw 102 (shown in FIG. 1). The wire positioning assembly 106 comprises the wire locking button 108 and the wire locking housing 110.

Further, the wire positioning assembly 106 comprises a wire anchor 400 for holding the surgical guide wire 104. The wire anchor 400 comprises a plurality of interior slots 402 disposed along a length of the wire anchor 400. The interior slots 402 are sized to receive a head 404 of the surgical guide wire 104. During assembly, the head 404 of the surgical guide wire 104 is inserted into one slot of the plurality of interior slots 402. Once inserted, the interior slot 402 secures the surgical guide wire 104 to the wire anchor 400. Indeed, a lip 406 of the head 404 of the surgical guide wire 104 may contact sidewalls 408 of the interior slot 402 once inserted such that the interface between the lip 406 and the sidewalls 408 restrains at least axial movement of the surgical guide wire 104 with respect to the wire anchor 400. Moreover, the head 404 may be inserted into a particular interior slot 402 based on a desired position of the surgical guide wire 104 with respect to the cannulated pedicle screw 102. Indeed, disposing the head 404 of the surgical guide wire 104 in a particular interior slot 402 of the plurality of interior slots 402 pre-positions the surgical guide wire 104 with respect to the cannulated pedicle screw 102.

The wire anchor 400 also comprises an interface surface 410 formed on an exterior of the wire anchor 400. Specifically, the interface surface 410 may be formed on a radially exterior surface 412 of the wire anchor 400. The interface surface 410 may include a plurality of anchor notches 414 formed along a length of the wire anchor 400. The interface surface 410 may be configured to interface with the wire locking button 108 to restrain axial movement of the wire anchor 400 with respect to the wire locking housing 110. As set forth above, the wire locking button 108 is actuatable between a locked position and an unlocked position to control an axial position of the surgical guide wire 104 conveyed through the with respect to the cannulated pedicle screw 102. As the surgical guide wire 104 is axially restrained with respect to the wire anchor 400 and the cannulated pedicle screw 102 may be axially restrained with respect to the wire locking housing 110, the interface between the wire locking button 108 and the wire anchor 400 may also restrain axial movement of the surgical guide wire 104 with respect to the cannulated pedicle screw 102.

In the illustrated embodiment, the wire locking button 108 is disposed in the locked position. In the locked position, the wire locking button 108 engages the interface surface 410 of the wire anchor 400 to restrain axial movement of the wire anchor 400. In particular, the wire locking button 108 may be configured to interface with an anchor notch 414 of the interface surface 410 in the locked position that is axially aligned with the wire locking button 108. That is, the shoulder 202 of the wire locking button 108 may be at least partially inserted into the axially aligned anchor notch 414 such that the sidewalls 204 of the shoulder 202 contact corresponding walls 416 of the axially aligned notch 414 to ultimately restrain movement of the surgical guide wire 104 with respect to the cannulated pedicle screw 102 in the locked position.

In some embodiments, the interface surface 410 of the wire anchor 400 may comprise a threaded exterior surface (not shown). The wire locking button 108 of the wire positioning assembly 106 may be configured to engage the threaded exterior surface to restrain movement of the wire anchor 400 with respect to the wire locking housing 110 in the locked position. Having a threaded exterior surface may allow for more controlled advancement of the surgical guide wire 104. For example, the wire position handle 112 may be secured to the wire anchor 400. As such rotation of the wire position handle 112 may rotate the wire anchor 400 with respect to the wire locking button 108. Such rotation may axially advance the wire anchor 400 via relative movement of the threads contacting the wire locking button 108.

Moreover, the wire positioning assembly 106 may include a secondary lock 418 attached to a distal end 420 of the wire anchor 400. The secondary lock 418 may be rotated and locked into place to prevent undesired motion of the surgical guide wire 104 or stylet.

Referring to FIG. 4B, the wire locking button 108 is disposed in the unlocked position. In the unlocked position, the wire locking button 108 releases the interface surface 410 of the wire anchor 400 such that the surgical guide wire 104 may slide axially with respect to the surgical instrument 100. In the unlocked position, the shoulder 202 is retracted from the axially aligned notch 414 of the interface surface 410 such that the shoulder 202 no longer contacts the corresponding walls 416 of the axially aligned notch 414 to ultimately restrain movement of the surgical guide wire 104 with respect to the cannulated pedicle screw 102 (shown in FIG. 1).

Figure 5:
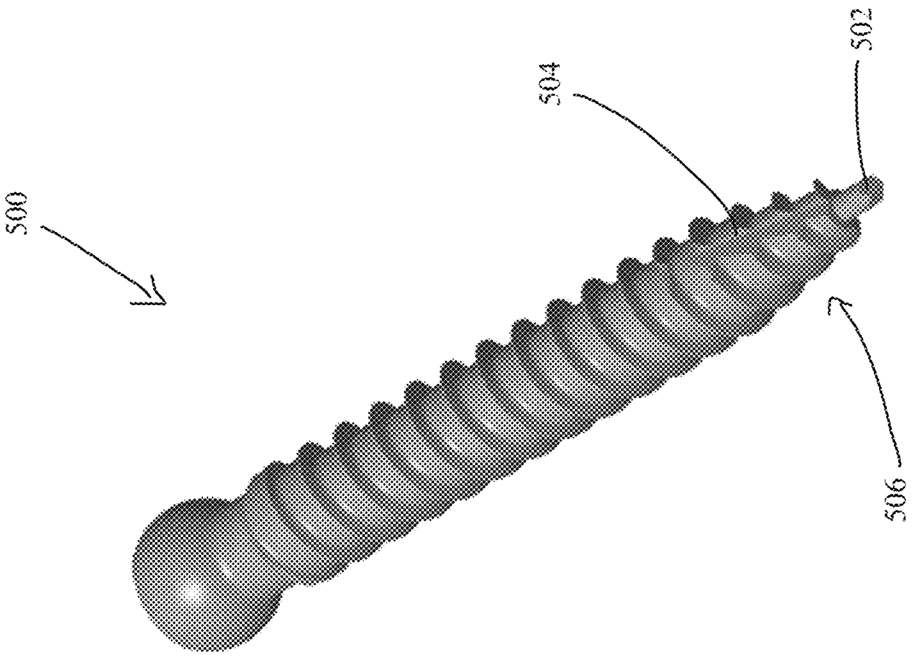
FIG. 5 illustrates a perspective view of a surgical guide wire embedded pedicle screw.

FIG. 5 illustrates a perspective view of a surgical guide wire embedded pedicle screw. As illustrated, the embedded pedicle screw 500 may have a guide wire 502 built into the embedded pedicle screw 500. Having the guide wire 502 embedded into the embedded pedicle screw 500 may eliminate the need for cannulated instrumentation while still providing an initial guide for placement of the embedded pedicle screw 500. That is, the embedded pedicle screw 500 may still be guided by the embedded guide wire 502 before committing to full screw implantation or insertion. For example, the embedded guide wire 502 may be used for docking the embedded pedicle screw 500 prior to insertion. The embedded pedicle screw 500 may then be inserted. After insertion, the embedded guide wire 502 may be retracted into the embedded pedicle screw 500. Indeed, the embedded pedicle screw 500 may include a spring system (not shown) configured to retract the embedded guide wire 502 after insertion. Moreover, the embedded pedicle screw 500 may include cutting flutes 504 on a tip 506 of the embedded pedicle screw 500 to prevent splitting of bone during the transition from the embedded guide wire 502 to the tip 506 of the embedded pedicle screw 500.

Figure 6:
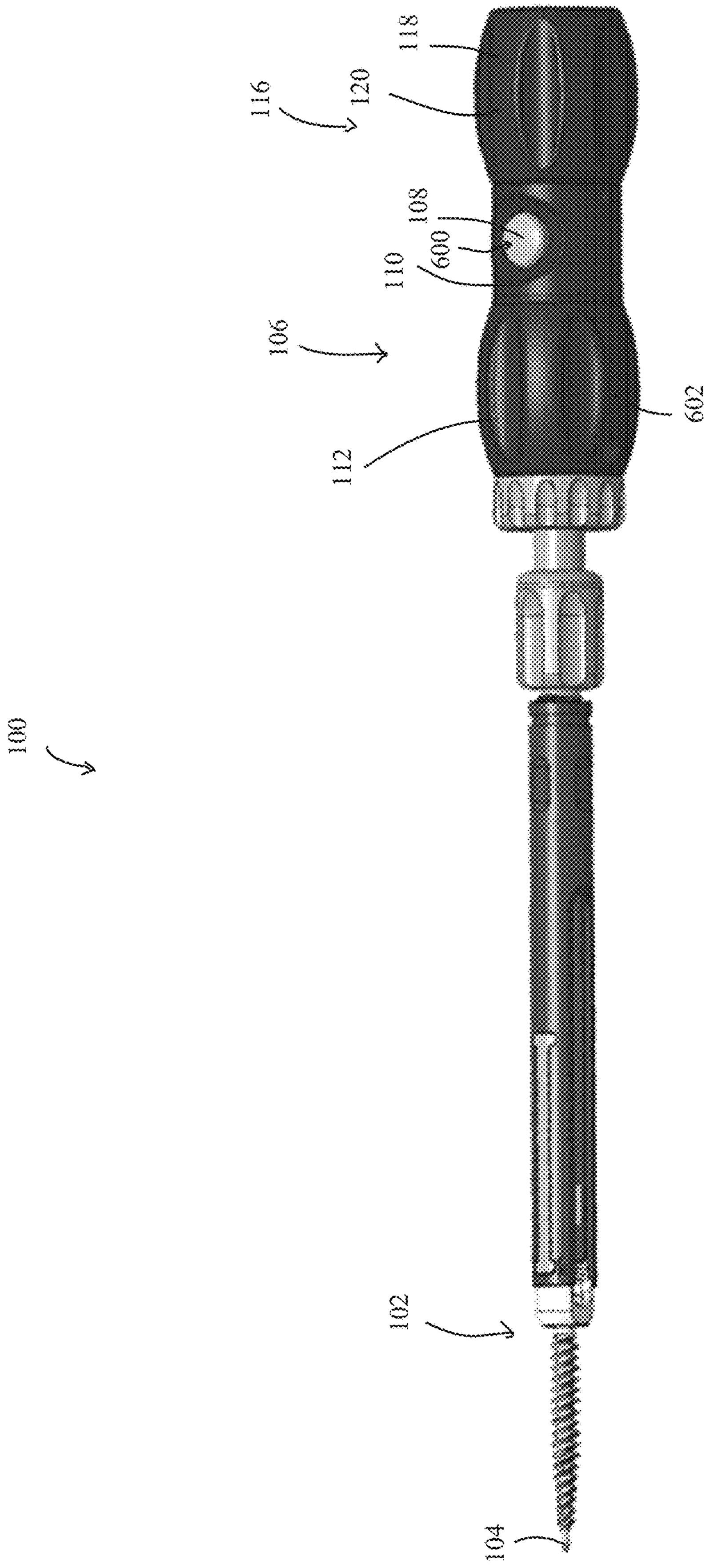
FIG. 6 illustrates a perspective view of another surgical instrument for inserting a cannulated pedicle screw and a surgical guide wire.

FIG. 6 illustrates a perspective view of another surgical instrument for inserting a cannulated pedicle screw and a surgical guide wire. As illustrated, the surgical instrument 100 includes the wire positioning assembly 106 for controlling movement of the surgical guide wire 104 with respect to the cannulated pedicle screw 102. The wire positioning assembly 106 may include a wire locking housing 110 and a locking mechanism 600 that is actuatable between the locked position and the unlocked position to restrain an axial position of the surgical guide wire 104 with respect to the cannulated pedicle screw 102. Specifically, the locking mechanism 600 may include the wire locking button 108. Pressing the wire locking button 108 may toggle the wire locking button 108 between the locked and unlocked positions. In the locked position, the wire locking button 108 may restrain free axial movement of the surgical guide wire 104 with respect to the cannulated pedicle screw 102. In the unlocked position, the surgical guide wire 104 may slide freely in the axial direction with respect to the cannulated pedicle screw 102.

The wire positioning assembly 106 further includes a positional adjustment mechanism 602 for adjusting an axial position of the surgical guide wire 104 conveyed through the respective through bores of the driver shaft (shown in FIG. 7) and the cannulated pedicle screw 102. In the illustrated embodiment, the positional adjustment mechanism 602 comprises a wire position handle 112 actuatable independent of the driver actuator 118. As set forth in greater detail below, actuation (e.g., rotation) of the wire position handle 112 is configured to move the surgical guide wire 104 with respect to the cannulated pedicle screw 102. That is, rotating the wire position handle 112 may extend and/or retract the surgical guide wire 104 with respect to the cannulated pedicle screw 102.

Further, the surgical instrument 100 may include the driver assembly 116 to advance the cannulated pedicle screw 102 along the surgical guide wire 104 and implant/drive the cannulated pedicle screw 102 into a bone (e.g., vertebra). During operation, the driver assembly 116 may be interfaced with the cannulated pedicle screw 102. With the surgical guide wire 104 inserted, to position and orient the cannulated pedicle screw 102 with respect to the vertebra, the driver assembly 116 is configured to drive the cannulated pedicle screw 102 into a vertebra (not shown). Specifically, the driver assembly 116 may have the driver shaft 700 (shown in FIG. 7) configured to couple to the cannulated pedicle screw 102. Although it is not shown in the illustrated embodiment, the driver shaft 700 may comprise a through bore for conveying the surgical guide wire 104. The surgical guide wire 104 may extend through the wire positioning assembly 106, the driver assembly 116, and the cannulated pedicle screw 102.

The driver assembly 116 may also include a driver actuator 118 coupled to the driver shaft 700. The driver actuator 118 is actuatable to rotate the driver shaft 700. As set forth above, the driver shaft 700 may be coupled to the cannulated pedicle screw 102 during operation. As such, rotating the driver shaft 700 may rotate the cannulated pedicle screw 102 to drive the cannulated pedicle screw 102 forward into the vertebra or target location. The driver actuator 118 may be actuatable independent of the wire position handle 112. Indeed, the driver actuator 118 may include a driver handle 120 configured to rotate to drive rotation of the driver shaft 700. However, any suitable mechanism may be used to drive rotation of the driver shaft 700.

Figure 7:
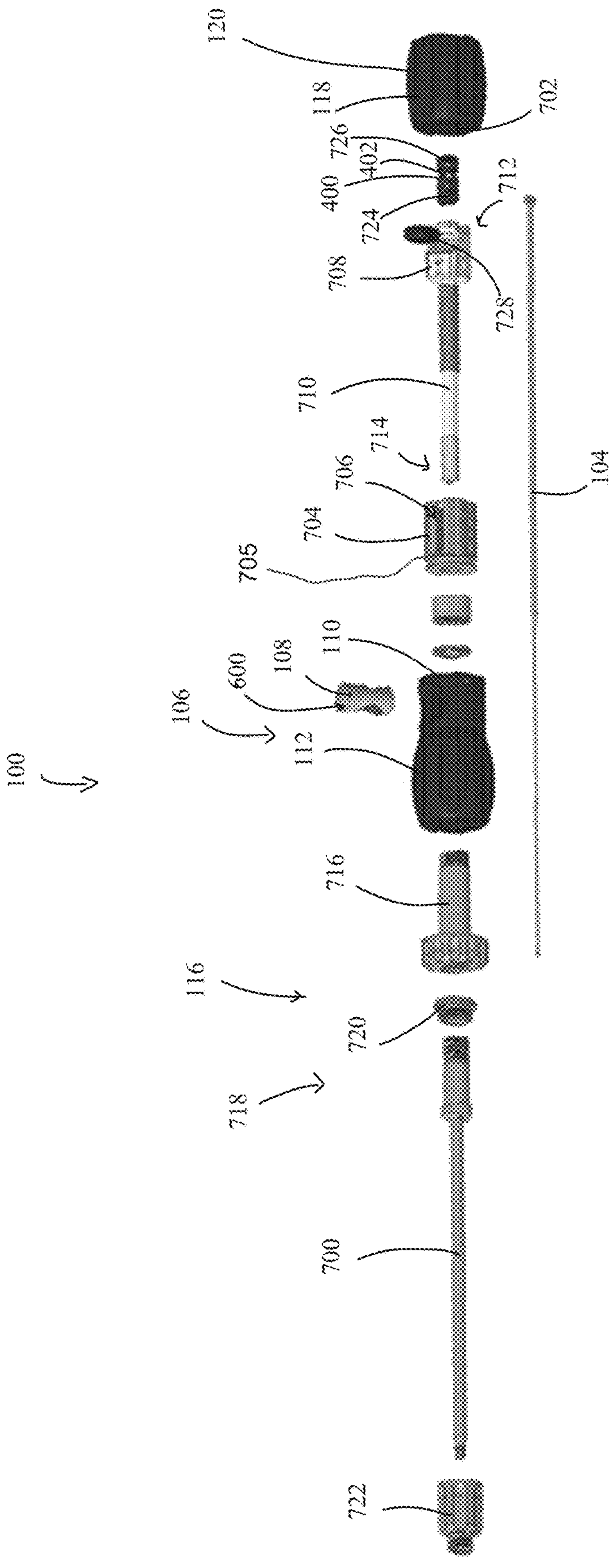
FIG. 7 illustrates an exploded view of the surgical instrument for inserting a cannulated pedicle screw and a surgical guide wire.

FIG. 7 illustrates an exploded view of the surgical instrument for inserting a cannulated pedicle screw and a surgical guide wire. As set forth above, the surgical instrument 100 includes the driver assembly 116 having the driver actuator 118, which is actuatable to drive rotation of the driver shaft 700. As illustrated, the driver actuator 118 may comprise a driver handle 120 configured to rotate to drive rotation of the driver shaft 700. The driver handle 120 may have an internal bore 702 for receiving a driver 704. An exterior surface 705 of the driver 704 is couplable to the driver actuator 118, via the internal bore 702, such that the rotational motion from the driver handle driver 704 is transferred to the driver 704. The internal bore 702 of the driver handle 120 and the exterior surface 706 of the driver 704 may include non-circular cross-sections. In the illustrated embodiment, the internal bore 702 of the driver handle 120 and the exterior surface 706 of the driver 704 each comprise substantially square-shaped cross-sections. However, the internal bore 702 and the exterior surface 706 may comprise any suitable cross-sections and/or shapes.

Moreover, the driver 704 may comprise an internal cavity 800 (shown in FIG. 8) for receiving a head portion 708 of a wire anchor housing 710. The internal cavity 800 of the driver 704 and the head portion 708 of the wire anchor housing 710 may also include non-circular cross-sections such that rotation of the driver 704 drives rotation of the wire anchor housing 710. The head portion 708 of the wire anchor housing 710 may be disposed at a proximal end 712 of the wire anchor housing 710. Further, a distal end 714 of the wire anchor housing 710 may be secured to a driver connector 716 such that rotation of the wire anchor housing 710 drives rotation of the driver connector 716. The driver connector 716 is coupled to the driver shaft 700 such that rotation of the driver connector 716 drives rotation of the driver shaft 700. The driver shaft 700 is couplable to the cannulated pedicle screw 102. Accordingly, rotation of the driver handle 120 ultimately drives rotation of the driver shaft 700 such that the surgical instrument 100 may advance the cannulated pedicle screw 102.

The surgical instrument 100 may also include a driver shaft coupler 718 configured to secure a removable tower portion 1106 (shown in FIG. 11) of the cannulated pedicle screw 102 to the driver shaft 700. The driver shaft coupler 718 may include an upper driver shaft coupler 720 interfaceable with an upper end of the removable tower portion 1106 and a lower driver shaft coupler 722 interfaceable with a lower end of the removable tower portion 1106. Each of the above-mentioned components (e.g., the driver 704, the wire anchor housing 710, the driver connector 716, the driver shaft 700, the lower driver shaft coupler 718, and the upper driver shaft coupler 718) may include respective through bores such that the surgical guide wire 104 may slide along a central axis of the surgical instrument 100 and through the cannulated pedicle screw 102.

The surgical instrument 100 also includes the wire positioning assembly 106 for advancing the surgical guide wire 104 with respect to the cannulated pedicle screw 102. As set forth above, the wire positioning assembly 106 comprises the wire position handle 112. Rotation of the wire position handle 112 may extend and/or retract the surgical guide wire 104 with respect to the cannulated pedicle screw 102. Further, the wire position handle 112 may be coupled with the wire locking housing 110 and the locking mechanism 600 (e.g., the wire locking button 108) may be housed in the wire locking housing 110. Moreover, the wire locking button 108 may be configured to interface with the wire anchor housing 710 such that rotation of the wire position handle 112 may rotate the wire anchor housing 710.

The wire anchor housing 710 is configured to receive the wire anchor 400. In particular, the head portion of the wire anchor housing 710 is formed to receive the wire anchor 400. Moreover, the wire anchor 400 is configured to secure the surgical guide wire 104. The wire anchor 400 may include the plurality of interior slots 402. A head portion 708 of the surgical guide wire 104 may be inserted into a desired slot of the plurality of interior slots 402 based on various factors including screw size. For example, the head portion 708 may be disposed in a distal slot 724 for a longer pedicle screw such that the surgical guide wire 104 is pre-positioned to extend out further with respect to the wire anchor 400. Disposing the head portion 708 in a proximal slot 726 may position the surgical guide wire 104 in a retracted position with respect to the distal slot 724. Additionally, the wire anchor 400 may be secured within the head portion 708 of the wire anchor housing 710 via a retention feature 728.

Figure 8:
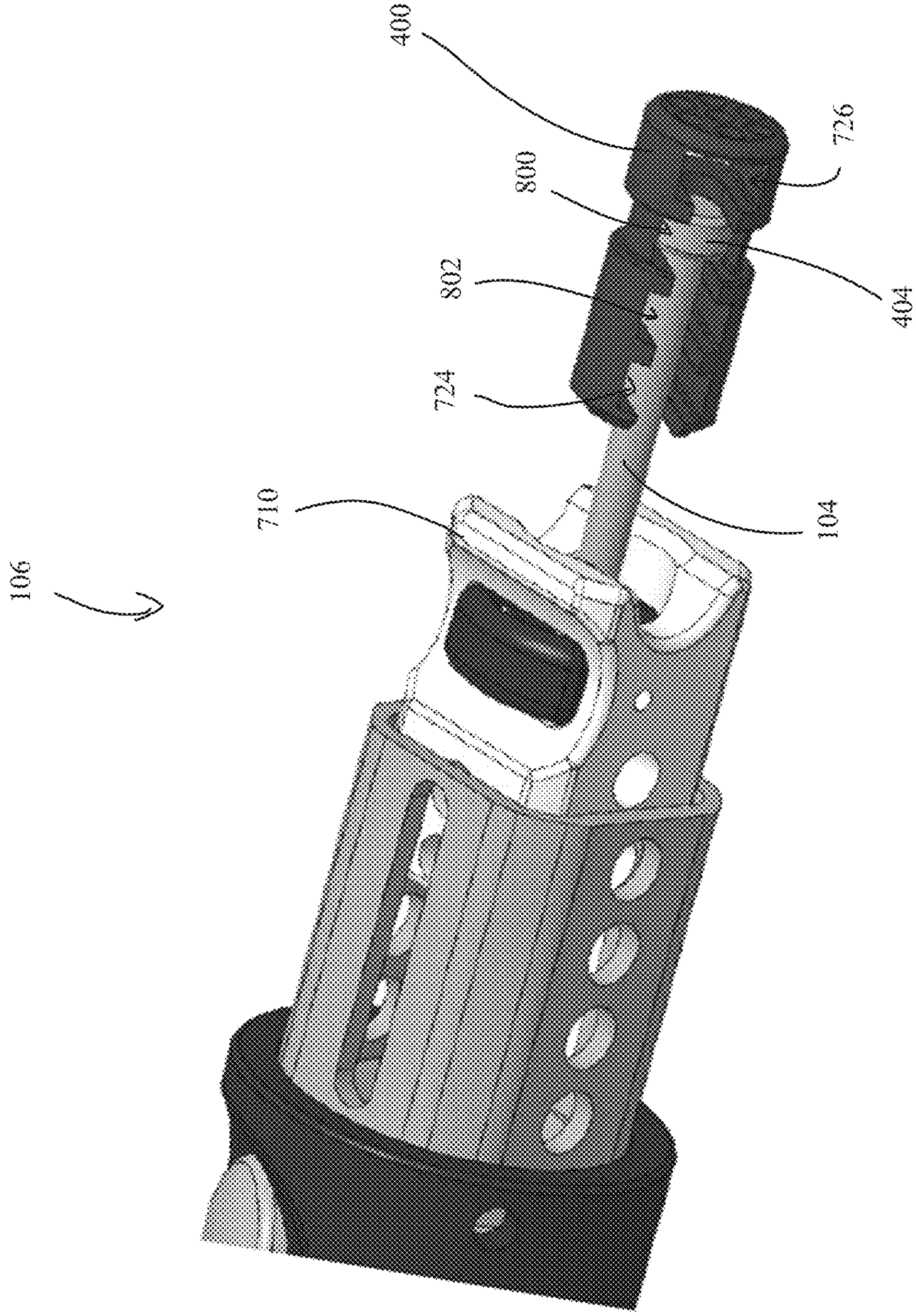
FIG. 8 illustrates a perspective view of another wire positioning assembly with the surgical guide wire coupled to a wire anchor and with the surgical guide wire partially inserted into a wire anchor housing.

FIG. 8 illustrates a perspective view of another wire positioning assembly 106 with the surgical guide wire 104 coupled to the wire anchor 400 and with the surgical guide wire 104 partially inserted into a wire anchor housing 710. As set forth above, the wire anchor 400 may include the plurality of interior slots 402 along a length of the wire anchor 400. In the illustrated embodiment, the wire anchor 400 comprises the proximal slot 726 (e.g., a first slot), a second slot 800, a third slot 802, and the distal slot 724 (e.g., a fourth slot) The head 404 of the surgical guide wire 104 is inserted into the second slot 800 of the plurality of interior slots 402. However, the head 404 may be positioned in any slot based on a desired guide wire pre-positioning for an operation. With the head 404 disposed the second slot 800, or any other desired slot, the surgical guide wire 104 may be axially secured to the wire anchor 400.

Figure 9:
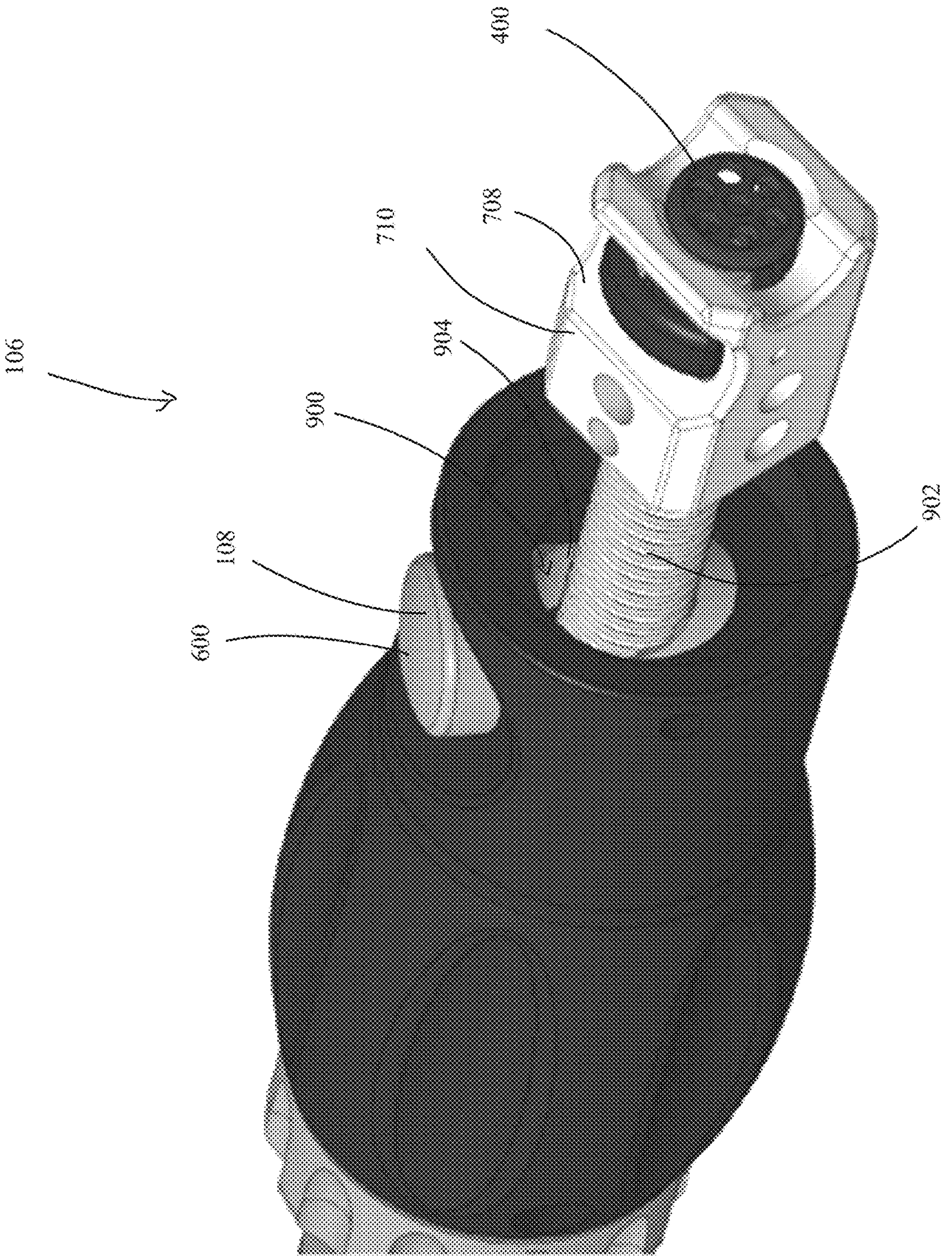
FIG. 9 illustrates a perspective view of the wire positioning assembly with the surgical guide wire and the wire anchor secured in the wire anchor housing.

FIG. 9 illustrates a perspective view of the wire positioning assembly 106 with the surgical guide wire and the wire anchor 400 secured in the wire anchor housing 710. As illustrated, the wire anchor housing 710 is disposed through an orifice 900 in the locking mechanism 600 (e.g., the wire locking button 108) such that the distal end 714 of the wire anchor housing 710 is disposed on an opposite side of the wire locking button 108 than the head portion 708 of the wire anchor housing 710. The wire anchor housing 710 may include a threaded portion 902 extending at least partially between the head portion 708 and the distal end 714 of the wire anchor housing 710. The threaded portion 902 may be configured to interface with an inner surface 904 of the orifice 900 of the locking mechanism 600. Such interface may mechanically couple the wire position handle 112 to the wire anchor housing 710.

Figure 10A:
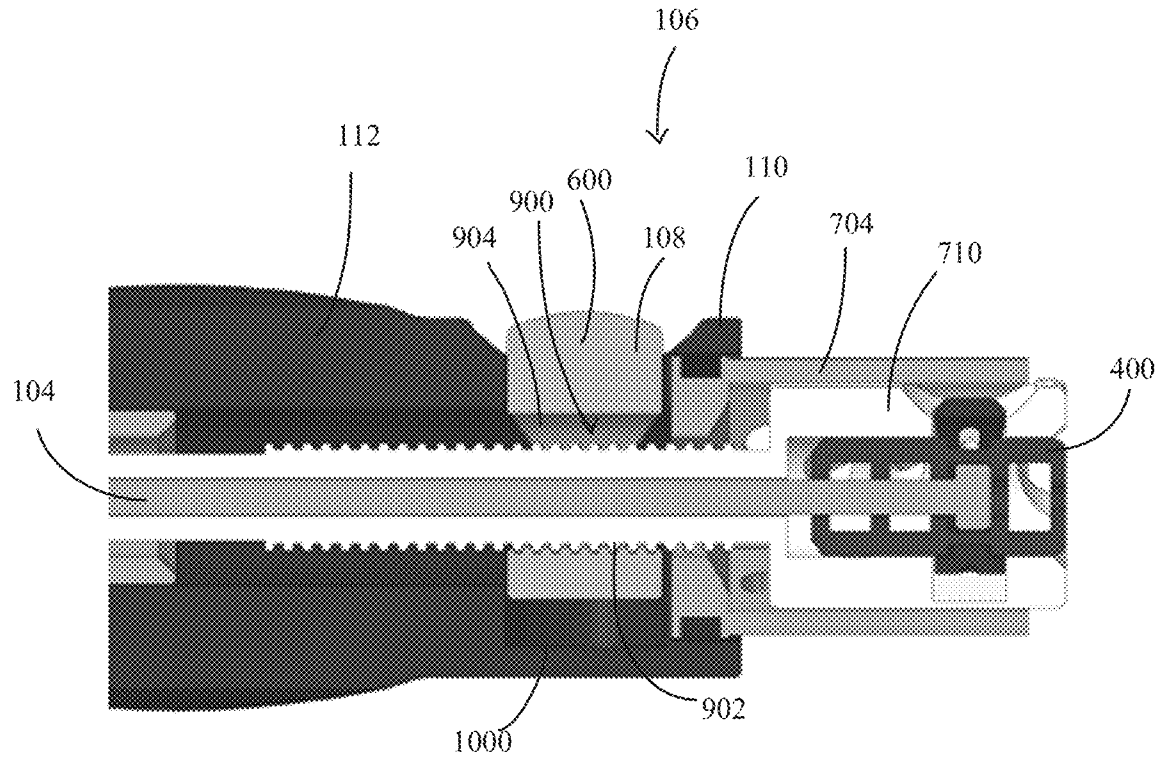
FIGS. 10A & 10B illustrate cross-sectional views of a wire locking button engaged and disengaged, respectively, with the wire anchor housing.
Figure 10B:
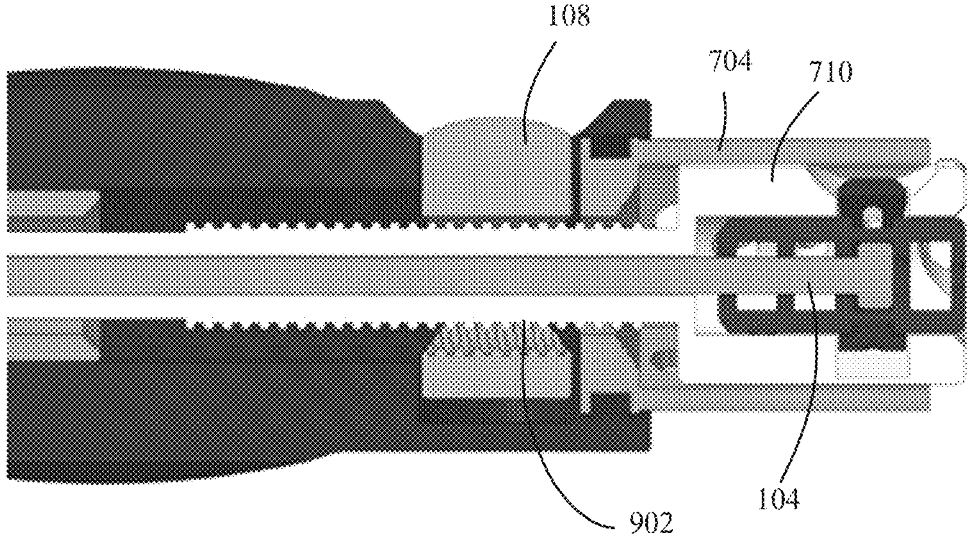

FIGS. 10A & 10B illustrate cross-sectional views of a wire locking button engaged and disengaged, respectively, with the wire anchor housing. As illustrated in FIG. 10A, the wire positioning assembly 106 comprises the wire position handle 112 coupled with the wire locking housing 110 and the locking mechanism 600 (e.g., the wire locking button 108) housed in the wire locking housing 110. The locking mechanism 600 may be toggled between a locked position and an unlocked position. In the locked position, the wire locking button 108 may be configured to interface with the wire anchor housing 710 such that rotation of the wire position handle 112 may advance the wire anchor housing 710 with respect to the driver 704. As set forth above, the wire anchor housing 710 is disposed within the driver 704 and may be slidable along the axial length of the driver 704. As the surgical guide wire 104 is secured to the wire anchor 400 housed in the wire anchor housing 710, sliding the wire anchor housing 710 may also slide the surgical guide wire 104 to extend and/or retract the with respect to the cannulated pedicle screw 102.

Moreover, the inner surface 904 of the orifice 900 of the wire locking button 108 may be threaded such that the wire locking button 108 may engage the threaded portion 902 of the wire anchor housing 710 in the locked position. During operation, the wire position handle 112 may be rotated while the driver handle (shown in FIG. 6) is held stationary. As such, the driver 704 may be held in place with respect to rotational movement. Further, the wire locking button 108 may rotate with respect to the driver 704. As the wire locking button 108 has a threaded interface with the wire anchor housing 710, rotation of the wire locking button 108 may pull the wire anchor housing 710 with respect to the driver 704 causing the wire anchor housing 710 to slide axially with respect to the driver 704. Such axial movement of the wire anchor housing 710 may move (e.g., extend) the surgical guide wire 104 axially with respect to the cannulated pedicle screw 102.

Moreover, the surgical instrument 100 may include a spring feature (not shown) interfaced with the wire locking button 108. The spring feature may be configured to bias the wire locking button 108 to remain in the locked position or the unlocked position. For example, the spring feature may include a compression spring disposed between the wire locking button 108 and an inner surface 1000 of the wire locking housing 110. Pressing the wire locking button 108 to the unlocked position may compress the spring feature such that the wire locking button 108 may rebound to the locked position when the wire locking button 108 is not actively pressed into the unlocked position. However, in some embodiments, the spring feature may be incorporated to toggle the wire locking button 108 between the locked position and the unlocked position.

Referring to FIG. 10B, the wire locking button 108 is positioned in the unlocked position. In the unlocked position, the wire locking button 108 disengages the threaded portion 902 of the wire anchor housing 710. Without the wire locking button 108 restraining movement of the wire anchor housing 710, the wire anchor housing 710 may slide freely with respect to the driver 704. During an operation, the wire locking button 108 may be moved to the unlocked position to quickly advance the surgical guide wire 104 with respect to the cannulated pedicle screw 102. For example, in the unlocked position, the wire anchor housing 710 may be pushed or malleted to advance the surgical guide wire 104. Once the surgical guide wire 104 is moved to a desired position, the wire locking button 108 may be moved to the locked position to re-engage the threaded interface between the wire locking button 108 and the wire anchor housing 710 to hold the surgical guide wire 104 in the desired position.

Figure 11A:
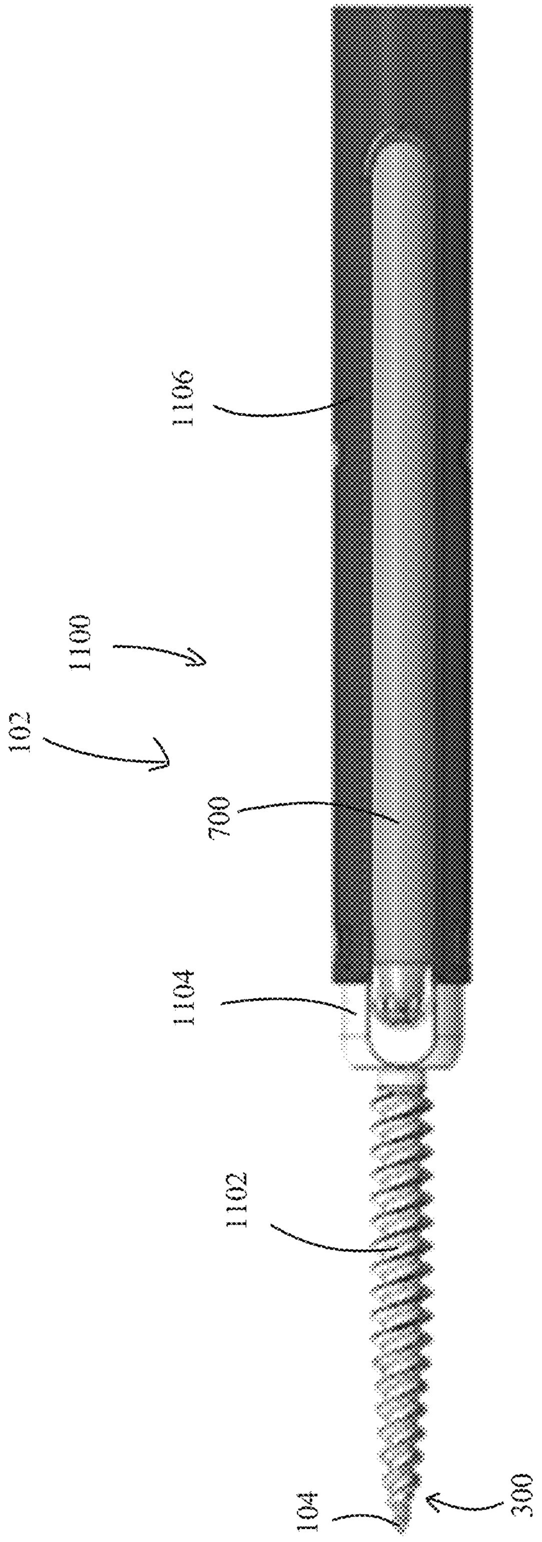
FIGS. 11A & 11B illustrate side views of a surgical guide wire in a retracted and an extended position, respectively, with respect to a cannulated pedicle screw tower.
Figure 11B:
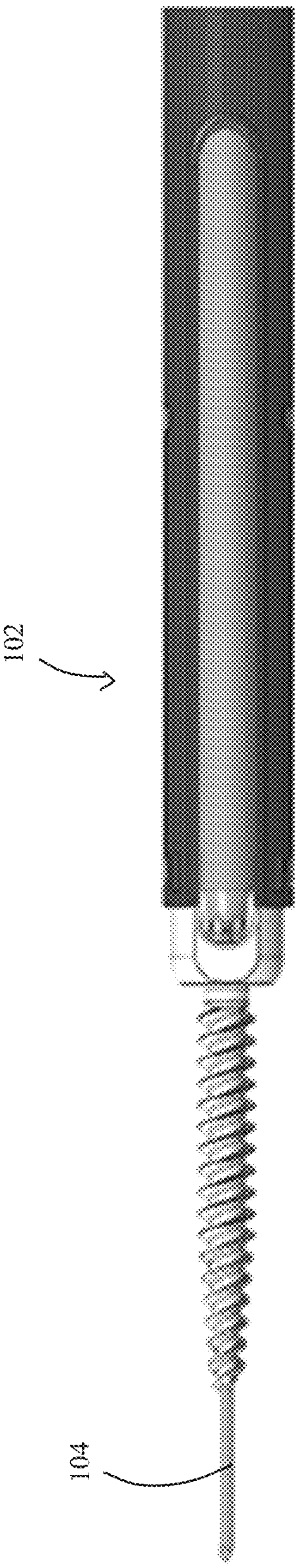

FIGS. 11A & 11B illustrate side views of a surgical guide wire in a retracted and an extended position, respectively, with respect to a cannulated pedicle screw tower. As illustrated in FIG. 11A, the cannulated pedicle screw 102 may comprise a cannulated pedicle screw tower 1100. The cannulated screw tower 1100 may include a screw portion 1102 for insertion into a target material (e.g., bone). The cannulated screw tower 1100 may also include a tulip portion 1104 secured to the screw portion 1102 and configured to provide attachment point for connection with adjacent cannulated pedicle screw towers via a surgical rod (not shown). Further, the cannulated screw tower 1100 may include a removable tower portion 1106 configured to detach from the tulip portion 1104 after insertion of the screw portion 1102 into the target material.

As set forth above, the cannulated pedicle screw 102 is configured to advance in response to rotation of the driver shaft 700. However, prior to implanting the cannulated pedicle screw 102, the surgical guide wire 104 may be extended or retracted relative to a tip 300 of the screw portion 1102 of the cannulated pedicle screw 102 via the wire positioning assembly. That is, the surgical guide wire 104 extending through the cannulated pedicle screw 102 may be extended or retracted. In the illustrated embodiment, the surgical guide wire 104 is in a retracted position with respect to the cannulated pedicle screw 102.

Referring to FIG. 11B, the surgical guide wire 104 is in an extended position with respect to the cannulated pedicle screw 102. As set forth above in FIGS. 10A and 10B, the wire positioning assembly 106 may further extend the surgical guide wire 104 by actuating the wire position handle 112. Further, the wire positioning assembly 106 may at least partially retract the surgical guide wire 104 by actuating the wire position handle 112 in an opposite direction. For example, rotating the wire position handle 112 clockwise may extend the surgical guide wire 104 and rotating the wire position handle 112 counterclockwise may retract the surgical guide wire 104. Alternatively, the wire locking button 108 may be moved to the unlocked position such that the surgical guide wire 104 may be pushed or pulled, directly or indirectly, to extend or retract the surgical guide wire 104.

In all disclosed embodiments, any handle may be easily detachable from the screw driver component via a button, locking clips, and the like such that it can adapt to various work flows including navigated, augmented reality, and traditional freehand, and also for improved cleaning properties.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A surgical instrument, comprising:

a driver shaft couplable to a cannulated pedicle screw and having a through bore for conveying a surgical guide wire through the cannulated pedicle screw;

a wire positioning assembly including a positional adjustment mechanism for adjusting an axial position of the surgical guide wire with respect to the cannulated pedicle screw and a locking mechanism for locking the axial position of the surgical guide wire; and a driver assembly including a driver actuator coupled to the driver shaft, wherein the driver actuator is operable to rotate the driver shaft to drive rotation of the cannulated pedicle screw, wherein the wire positioning assembly includes a second lock attached to a distal end of a wire anchor.

2. The surgical instrument of claim 1, further comprising the surgical guide wire, wherein the surgical guide wire is releasably securable via the locking mechanism.

3. The surgical instrument of claim 2, wherein the surgical guide wire comprises a plurality of notches axially spaced along a portion of the surgical guide wire, and wherein the locking mechanism comprises a wire locking button that interfaces with at least one notch of the plurality of notches in the locked position to restrain axial movement of the surgical guide wire with respect to the driver shaft.

4. The surgical instrument of claim 1, wherein the driver actuator comprises a driver handle rotatable to drive rotation of the driver shaft.

5. The surgical instrument of claim 1, wherein the positional adjustment mechanism comprises a wire position handle actuatable independent of the driver handle, and wherein actuation of the wire position handle moves the surgical guide wire with respect to the cannulated pedicle screw.

6. The surgical instrument of claim 1, wherein the positional adjustment mechanism comprises a wire position handle rotatable to drive axial movement of the surgical guide wire with respect to the wire position handle via a threaded connection with the surgical guide wire, wherein surgical guide wire comprises first threads, and wherein the locking mechanism includes a wire locking button comprising second threads that are engageable with the first threads of the surgical guide wire in the locked position and that are disengageable with the first threads in the unlocked position.

7. The surgical instrument of claim 1, wherein the wire anchor includes a plurality of slots disposed along a length of the wire anchor, wherein each slot of the plurality of slots is formed to receive a head of the surgical guide wire to axially secure the surgical guide wire to the wire anchor.

8. The surgical instrument of claim 7, wherein the wire anchor comprises a plurality of notches formed on an exterior surface of the wire anchor, and wherein the wire positioning assembly selectively engages at least one notch of the plurality of notches to restrain movement of the wire anchor with respect to the driver shaft in the locked position.

9. The surgical instrument of claim 7, wherein the wire anchor comprises a threaded exterior surface, and wherein the wire positioning assembly is engageable with the threaded exterior surface to restrain movement of the wire anchor with respect to the driver shaft in the locked position.

10. The surgical instrument of claim 7, further comprising a wire anchor housing formed to house the wire anchor, wherein the wire anchor housing comprises a threaded exterior portion interfaceable with a wire locking button of the wire positioning assembly.

11. The surgical instrument of claim 10, wherein the wire locking button is rotatable about the wire anchor housing, and wherein rotation of the wire locking button drives axial movement of the wire anchor housing.

12. The surgical instrument of claim 10, wherein the wire locking button is radially actuatable between the unlocked position and the locked position, wherein the wire locking button is disengaged from the threaded exterior portion of the wire anchor housing in the unlocked position.

13. The surgical instrument of claim 10, further comprising a retention feature interfaceable with the wire anchor and the wire anchor housing to axially secure the wire anchor within the wire anchor housing.

14. The surgical instrument of claim 10, further comprising a driver comprising a central bore for housing a wire anchor housing, wherein the wire anchor housing is slidable within the driver, and wherein an exterior surface of the driver is couplable to the driver actuator such that the driver transfers rotational motion from the driver actuator.

15. The surgical instrument of claim 1, further comprising a driver connector coupled to the driver shaft, wherein the rotational motion of the driver actuator drives rotation of the driver connector, and wherein rotation of the driver connector drives rotation of the driver shaft.

16. A surgical instrument, comprising:

a surgical guide wire having a plurality of notches axially spaced along a portion of the surgical guide wire;

a driver shaft couplable to a cannulated pedicle screw, wherein the driver shaft comprises a through bore for conveying the surgical guide wire through the cannulated pedicle screw;

a driver actuator coupled to the driver shaft, wherein the driver actuator is operable to rotate the driver shaft to drive rotation of the cannulated pedicle screw;

a wire positioning assembly comprising a first locking mechanism and a second locking mechanism, wherein the first locking mechanism is actuatable between a locked position and an unlocked position to control an axial position of the surgical guide wire conveyed through the through bore of the driver shaft and the cannulated pedicle screw, and a second lock mechanism attached to a distal end of a wire anchor.

17. A surgical instrument, comprising:

a driver shaft couplable to a cannulated pedicle screw, wherein the driver shaft comprises a through bore for conveying a surgical guide wire;

a driver actuator coupled to the driver shaft, wherein the driver actuator is actuatable to rotate the driver shaft;

a wire anchor having a plurality of interior slots disposed along a length of the wire anchor, wherein each slot of the plurality of interior slots is formed to receive a head of the surgical guide wire to axially secure the surgical guide wire to the wire anchor, wherein disposing the head of the surgical guide wire in a particular slot of the plurality of interior slots pre-positions the surgical guide wire, and wherein the wire anchor comprises an interface surface formed on an exterior of the wire anchor; and a wire locking button actuatable between a locked position and an unlocked position to control an axial position of the surgical guide wire conveyed through the through bore of the driver shaft and the cannulated pedicle screw, and wherein the wire locking button engages the interface surface of the wire anchor in the locked position to restrain axial movement of the wire anchor with respect to the driver shaft, and wherein the wire locking button releases the interface surface of the wire anchor in the unlocked position;

wherein a second lock mechanism is attached to a distal end of a wire anchor.

* * * * *